United States Patent [19]

Evans et al.

[11] Patent Number: 5,571,723
[45] Date of Patent: Nov. 5, 1996

[54] METHOD OF TESTING FOR DIABETES THAT REDUCES THE EFFECT OF INTERFERING SUBSTANCES

[76] Inventors: Cody A. Evans, 28 Innisbrook Ave., Las Vegas, Nev. 89113; Harold M. Bates, 4 Barnes Ct., East Brunswick, N.J. 08816

[21] Appl. No.: 56,993

[22] Filed: May 3, 1993

Related U.S. Application Data

[63] Continuation-in-part of Ser. No. 651,768, Feb. 7, 1991, abandoned, and Ser. No. 14,060, Feb. 5, 1993, abandoned, which is a continuation of Ser. No. 795,990, Nov. 22, 1991, abandoned, which is a continuation-in-part of Ser. No. 651,768, Feb. 7, 1991, abandoned.

[51] Int. Cl.$^6$ .................... G01N 33/49; G01N 1/18
[52] U.S. Cl. .................... 436/87; 436/14; 436/88; 436/95; 436/175; 436/177; 436/811; 436/904
[58] Field of Search .................... 436/12, 14, 16, 436/87, 88, 99, 811, 904, 175, 95, 177

[56] References Cited

U.S. PATENT DOCUMENTS

| | | |
|---|---|---|
| 2,981,606 | 4/1961 | Keston . |
| 3,576,815 | 4/1971 | Doyle . |
| 3,653,841 | 4/1972 | Klein . |
| 3,657,071 | 4/1972 | BergMeyer et al. .................... 435/193 |
| 3,682,586 | 8/1972 | Ertingshausen et al. . |
| 3,791,988 | 2/1974 | Pratteln et al. . |
| 3,920,580 | 11/1975 | Mast . |
| 4,200,435 | 4/1980 | Stroupe et al. . |
| 4,243,534 | 1/1981 | Bulbenko . |
| 4,260,516 | 4/1981 | Moore . |
| 4,268,270 | 5/1981 | Gabbay et al. . |
| 4,269,605 | 5/1981 | Dean et al. . |
| 4,371,374 | 2/1983 | Cerami . |
| 4,397,956 | 8/1983 | Maggio .................... 436/34 |
| 4,399,227 | 8/1983 | Niederau et al. . |
| 4,407,961 | 10/1983 | Sanders . |
| 4,409,335 | 10/1983 | Hanamoto et al. . |
| 4,627,014 | 12/1986 | Lo et al. . |
| 4,642,295 | 2/1987 | Baker .................... 436/87 |
| 4,645,742 | 2/1987 | Baker . |
| 4,797,473 | 1/1989 | Tarsio et al. . |
| 4,956,301 | 9/1990 | Ismail et al. .................... 436/87 |
| 5,002,893 | 3/1991 | Rosenthal . |
| 5,055,388 | 10/1991 | Vogt et al. .................... 436/904 X |
| 5,110,745 | 5/1992 | Kricka et al. . |
| 5,132,230 | 7/1992 | Rosenthal et al. . |

FOREIGN PATENT DOCUMENTS

| | | |
|---|---|---|
| 0085263 | 8/1983 | European Pat. Off. . |
| 215170 | 3/1987 | European Pat. Off. . |
| 0215170 | 3/1987 | European Pat. Off. . |
| 63-180861 | 7/1988 | Japan . |
| 1322951 | 7/1973 | United Kingdom . |
| 2101740 | 1/1983 | United Kingdom . |
| WO82/01804 | 5/1982 | WIPO . |

OTHER PUBLICATIONS

R. Miksch et al *Chem. Abst.* 1973, 79, 50475K.
D. Juretic et al. *Chem. Abstr.* 1986, 104, 17258d.

(List continued on next page.)

*Primary Examiner*—Arlen Soderquist
*Attorney, Agent, or Firm*—Bryan Cave, LLP

[57] ABSTRACT

An improved method of testing individuals for diabetes, even if they have levels of interfering substances (e.g., uric acid, bilirubin, and glutathione) that would otherwise interfere with such testing, is disclosed. The individual's protein-bound glucose level and glucose level are compared to the analogous values for a reference population to enable the risk of that individual's having diabetes to be assessed. The substances that would otherwise tend to interfere with the assay for protein-bound glucose are removed before the assay, desirably by precipitating the protein-bound glucose using uranyl acetate, which desirably leaves substantially all of the interfering substances in the supernatant, then separating the precipitate from the supernatant, redissolving the precipitate, and conducting the colorimetric assay on the resulting solution. An improved colorimetric test for protein-bound glucose using viologens as the colorimetric electron acceptors is also disclosed.

21 Claims, 1 Drawing Sheet

OTHER PUBLICATIONS

D. Juretic et al. *Z. Med. Laboratoriumsdiagn.* 1987, 28, 316–319.

H. J. Wildgrube et al. *Chem. Abstr.* 1972, 77, 16117u.

D. G. Gardiner *Anal. Biochem.* 1979, 95, 377–382.

A. Ma et al. *Clin. Chim. Acta* 1981, 115, 111–117.

D. Juretic et al. *Chem. Abstr.* 1987, 107, 194476f.

F. Heepe et al. *Klin. Worchsohr.* 1957, 35, 390–393.

L. Michaelis et al. *Chem. Abstr.* 1934, 28, 1709.

K. Dirr et al. *Hoppe–Seylers Z. Physiol. Chem.* 1957, 307, 97–102.

R. F. Homer et al. *Nature* 1959, 184, 2012–2013.

D. N. Kramer et al. *J. Org. Chem. 1967, 32, 1163–1165.*

P. Fonty *Feuill. Biol.* 1969, 10, 53–55.

P. A. Trudinger *Anal. Bio Chem.* 1970, 36, 222–225.

R. Schlaeger et al. *Z. Klin. Chem. Klin. Biochem.* 1971, 9, 178–79.

G. E. Hoffmann et al. *J. Clin. Chem. Clin. Biochem.* 1980, 18, 129–132.

J. Boratynski *Anal. Biochem.* 1987, 160, 35–38.

D. A. Armbruster *Clin. Chem.* 1987, 33, 2153–2163.

S. A. Kretchmer et al. *Biochim. Biophys. Acta* 1988, 956, 85–94.

D. D. Koch *Laboratory Medicine* 1990, 21, 497–503.

Armbruster, "Fructosamine: Structure, Analysis, and Clinical Usefulness, " *Clin. Chem.*, vol. 33, No. 12, pp. 2153–2163 (1987).

Armbruster, "Diabetes Mellitus, Protein Glycation, and Laboratory Assays for Monitoring Long–Term Glycemic Control, " *Clin. Lab. Sci.* vol. 3, No. 3, pp. 184–188 (May/Jun. 1990).

Caines et al., "Colorimetric Determination of Non–Enzymatically Glycated Albumin, " *Clin. Biochem.*, vol. 19, pp. 26–30 (Feb. 1986).

Dolhofer et al., "Improvement of the thiobarbituric acid assay for serum glycosylprotein determination, " *Clinica Chima Acta*, vol. 112, pp. 197–204 (1981).

Hodge, "Dehydrated Foods Chemistry of Browning Reactions in Model Systems, " *Agricultural And Food Chemistry*, vol. 1, No. 15, pp. 928–943 (Oct. 14, 1953).

Ingles, "Thiol interaction in sugar–amine systems," *Chem. Abstr.* vol. 60, entry 6913g (Carbohydrates, 1964).

R. Dolhofer and O. H. Wieland, "Glycosylation of Serum Albumin: Elevated Glycosyl–Albumin In Diabetic Patients, " *FEBS Letters*, vol. 103, No. 2, pp. 282–286 (Jul. 1979).

R. Dolhofer, R. Renner, and O.H. Wieland, "Different Behavior of Haemoglobin $A_{Ia-c}$ and Glycosyl–Albumin Levels During Recovery from Diabetic Ketoacidosis and Nonacidotic Coma, " *Diabetologia*, vol. 21, pp. 211–215 (1981).

R. Dolhofer and O. H. Wieland, "Increased Glycosylation of Serum Albumin in Diabetes Mellitus, " *Diabetes*, vol. 29, pp. 417–422 (Jun. 1980).

Isolab Inc. brochure, *Isolines*, vol. 19, No. 3, 8 pages (Oct. 1990).

Johnson et al., "Fructosamine: a new approach to the estimation of serum glycosylprotein An index of diabetic control, " *Clinica Chimica Acta*, vol. 127, pp. 87–95 (1982).

Josef et al., "Composition for glucose determination," *Chem. Abstr.* vol. 82, entry 70120f (Biochem. Meth., 1975).

Jue et al., "Determination of reducing sugars in the nanomole range with tetrazolium blue, " *J. Biochem. Biosphys. Meth.*, vol. 11, pp. 109–115 (1985).

Mattson et al., "Colorimetric Determination of Reducing Sugars with Triphenyltetrazolium Chloride, " *Anal. Chem.* vol. 22, No. 1, pp. 182–185 (Jan. 1950).

Northcote, "Polysaccharides, " *Chem. Abstr.*, vol. 61, entry 14944g (1964).

Mopper et al., "A New Chromatographic Sugar Autoanalyzer with a Sensitivity of $10^{-10}$ Moles, " *Anal. Biochem.*, vol. 45, pp. 147–153 (1972).

Robin et al., "Automatic assay of reducing sugars using tetrazolium blue. Applications of gel–permeation chromatography, " *Chem. Abstr.*, vol. 95, entry 148753e (Foods, 1981).

Roche Diagnostic Systems, Inc. brochure, "RoTAG FRUCTOSAMINE (Glycated Protein) Assay, " 8 pages (Mar. 1988).

Roche Diagnostic Systems, Inc. package insert, "RoTAG Fructosamine (Glycated Protein) Assay, " 4 pages (Apr. 1988).

Rosenthal et al., "Evaluation of a Single–Color–Reading Method for Determining Fructosamine, " *Clin. Chem.*, vol. 34, No. 2, pp. 360–363 (1988).

Schleicher et al., "Specific Quantitation by HPLC of Protein (Lysine) Bound Glucose in Human Serum Albumin and Other Glycosylated Proteins, " *J. Clin. Chem. Clin. Biochem.*, vol. 19, pp. 81–87 (1981).

Trudinger, "On the Absorbancy of Reduced Methyl Violögen, " *Anal. Biochem.*, vol. 36, pp. 222–224 (1970).

Windeler et al., "The Fructosamine Assay in Diagnosis and Control of Diabetes mellitus Scientific Evidence for its Clinical Usefulness? , " *J. Clin. Chem. Clin. Biochem.*, vol. 28, pp. 129–138 (1990).

D. Koch, "Fructosamine: How Useful Is It?, " *Lab. Med.* vol. 21, No. 8, pp. 497–503 (Aug. 1990).

S. Asano. "Determination of fructosamine using electron transporter–containing reagent, " *Chem. Abstr.*, vol. 114, entry 243909e (Biochem. Meth. 1991).

J. Baker et al., "Fructosamine Test–Plus, a Modified Fructosamine Assay Evaluated, " *Clin. Chem.*, vol. 37, No. 4, pp. 552–556 (1991).

H. Brauner et al., "Glukosebestimmung–Stand und Perspektiven, " *Biomedizinische Technik*, Band 25, Heft 1–Feb. 1980, pp. 26–31 (1980).

Mashiba et al., "Measurement of glycated albumin by the nitroblue tetrazolium colorimetric method, " *Clinica Chimica Acta*, vol. 212, pp. 3–15 (1992).

Bunn, "Nonenzymatic Glycosylation of Protein: Relevance to Diabetes, " *Am. J. Med.*, vol. 70, pp. 325–330 (1981).

Tchobroutsky, "Blood glucose levels in diabetic and non––diabetic subjects, " *Diabetologia*, vol. 34, pp. 67–73 (1991).

Rosen, "Protein–Bound Glucose as a Screening Test for Diabetes, " *Hospital Practice*, vol. 27, Supplement 1, pp. 59–61 (1992).

Hodge, "The Amadori Rearrangement, " *Advances In Carbohydrate Chemistry* (edited by Wolfrom et al.), vol. 10, pp. 169–205 (1955).

Schleicher et al., "Protein Glycation: Measurement and Clinical Relevance, " *J. Clin. Chem. Clin. Biochem.*, vol. 27, pp. 577–587 (1989).

Cohen, "Measurement of Circulating Glycated Proteins to Monitor Intermediate–Term Changes in Glycaemic Control, " *Eur. J. Clin. Chem. Clin. Biochem.*, vol. 30, pp. 851–859 (1992).

Koskinen e tal., "Blood glycated haemoglobin, serum fructosamine, serum glycated albumin and serum total glycated total protein as measures of glycaemia in diabetes mellitus," *Scand. J. Clin. Lab. Invest.*, vol. 52, pp. 863–869 (1992).

Smith et al., "Preparation and characterisation of $N_E$(1–deoxy–D–fructos–1–y)hippuryl–lysine," *Carbohydrate Research*, vol. 223, pp. 293–298, (1992).

Hill et al., "Recommendations for adopting standard conditions and analytical procedures in the measurement of serum fractosamine concentration," *Ann. Clin. Biochem.*, vol. 27, pp. 413–424 (1990).

FIG. 1

METHOD OF TESTING FOR DIABETES THAT REDUCES THE EFFECT OF INTERFERING SUBSTANCES

RELATED APPLICATIONS

This application is a continuation-in-part of (a) U.S. application Ser. No. 07/651768, filed Feb. 7, 1991, and (b) U.S. application Ser. No. 08/014060, filed Feb. 5, 1993, which is a continuation of U.S. application Ser. No. 07/795990, filed Nov. 22, 1991, which is a continuation-in-part of U.S. application Ser. No. 07/651768, filed Feb. 7, 1991, all by the same inventors and all of which applications are hereby incorporated by reference in their entireties for all purposes and all of which are now abandoned.

BACKGROUND OF THE INVENTION

This invention relates to an improved test for diabetes mellitus ("diabetes") that can be used even with a patient having levels of substances that would otherwise interfere with testing, e.g., elevated (high) uric acid/and or bilirubin levels. Broadly speaking, this invention concerns a method of testing that treats a specimen from an individual to substantially reduce or eliminate interfering substances from the specimen, assays a material derived from the treated specimen for a certain clinical value (protein-bound glucose level), obtains a second clinical variable for that individual (glucose level), and then uses those two clinical values to assess the likelihood of that individual having diabetes, e.g., by placing the individual in any one of several categories, which categories are associated with pre-established risks of having diabetes.

As is well known, diabetes is a serious disease affecting a significant portion of the population. Detecting whether an individual has diabetes and monitoring diabetes therapy are some of the problems confronting medicine. An early screening test for diabetes and one that is still commonly used involves determining an individual's blood glucose level. See, e.g., U.S. Pat. Nos. 2,981,606; 3,653,841; 3,791,988; and 3,920,580 (all of the patent and other documents, including literature articles, cited or otherwise identified in this application are hereby incorporated herein in their entireties for all purposes). Glycosylated amino acids in urine have also been used to screen for diabetes. See U.S. Pat. No. 4,371,374. U.S. Pat. No. 4,397,956 concerns a single-reading pseudo-kinetic method for monitoring the status of control of ketoacidosis-prone diabetics by measuring the blood glucose and at least one additional indicator analyte (e.g., ketone bodies such as acetone, beta-hydroxybutyrate, and acetoacetate and fatty acid derivatives).

One problem with glucose tests is that even in an individual who does not have diabetes, his or her glucose level can vary over a wide range, depending on when the test sample or specimen (e.g., blood) was taken and when and what the individual last ate. Furthermore, even if one glucose test gives a high enough reading to strongly suggest the presence of diabetes, that individual must undergo additional tests, for example, a so-called glucose tolerance test, before a diagnosis of diabetes can be confirmed. The glucose level of a diabetic taking insulin can also vary dramatically depending upon when the individual last took insulin and on the dosage. It is not unknown for individuals who have diabetes to take insulin shortly before specimens are taken from them for therapy-monitoring glucose tests, so that their glucose tests will indicate normal levels of glucose and make it appear that the individuals have been conscientiously following their prescribed regimens of insulin therapy. That makes monitoring such therapy more difficult. For all these reasons, glucose testing alone was and is known to have significant disadvantages.

Reactions of sugars and amino compounds (for example, proteins) to form N-substituted glycosylamines, which undergo subsequent irreversible Amadori rearrangement, have been known for decades. See, e.g., Hodge, *Agricultural And Food Chemistry*, vol. 1, no. 15, pp. 928–943 (Oct. 14, 1953). Hodge also noted at p. 930 that investigators showed that glucose and the free amino groups of bovine serum albumin and other proteins and peptides combined in a one-to-one molar ratio.

Years ago it was discovered that in a human diabetic, hemoglobin reacts with glucose in the blood to produce glycated (glycosylated) hemoglobin and that the level of glycated hemoglobin can be determined and used to detect diabetes and to monitor the course of therapy. Hemoglobin is the most abundant protein found in whole blood and its half-life is about 60 days. Glycated hemoglobin forms when glucose binds to the amino moieties of the hemoglobin. The bound glucose moiety undergoes Amadori rearrangement to form a fructose moiety. Both glucose and fructose are reducing sugars, that is, they can reduce other compounds (donate electrons to the other compounds) under the appropriate reaction conditions. Because of the relatively lengthy half-life of hemoglobin, glycated hemoglobin is insensitive to short-term variations in glucose levels, such as might be caused by taking a large dose of insulin or eating sugar-containing candy. Thus, it was discovered that the glycated hemoglobin level indicated an individual's long-term blood glucose history. See, e.g., U.S. Pat. Nos. 4,200,435; 4,243,534; 4,260,516; 4,268,270; 4,269,605; 4,399,227; 4,407,961; and 4,409,335.

There are other proteins in blood besides hemoglobin, and years ago it was discovered that in a diabetic those other proteins also become glycated to a greater or lesser degree. Those proteins are reported to have half-lives of anywhere from 2.5 to 23 days. In particular, the half-life of albumin is reported to be 14 to 20 days and will be taken as 19 days for purposes of further discussion. Albumin (at about 35–50 grams per liter) and globulins (at about 20–30 grams per liter) are the principal proteins in serum. (Removal of blood cells from whole blood yields plasma, and coagulation of the fibrinogen in the plasma and removal of the resulting fibrin yields serum.) When serum proteins are glycated in vivo, glycated albumin usually accounts for about 80 percent of the glycated serum proteins (that is, protein-bound glucose).

Accordingly, detection of serum glycated proteins (sometimes called "fructosamines" in the literature) became another suggested method for detecting diabetes and monitoring its therapy. See, for example, U.S. Pat. Nos. 4,642,295; 4,645,742; 4,797,473; 4,956,301; 5,055,388; Japan Patent Application No. 63-180861; Schleicher et al., *J. Clin. Chem. Clin. Biochem.*, vol. 19, pp. 81–87 (1981); Dolhofer et al., *Clinica Chimica Acta*, vol. 112, pp. 197–204 (1981); Johnson et al., *Clinica Chimica Acta*, vol. 127, pp. 87–95 (1982); Armbruster, *Clin. Chem.*, vol. 33, no. 12, pp. 2153–2163 (1987); Rosenthal et al., *Clin. Chem.*, vol. 34, no. 2, pp. 360–363 (1988); Caines et al., *Clin. Biochem.*, vol. 19, pp. 26–30 (February. 1986); Jue et al., *J. Biochem. Biophys. Meth.*, vol. 11, pp. 109–115 (1985); Armbruster, *Clin. Lab. Sci.*, vol. 3, no. 3, pp. 184–188 (May/June 1990); and Windeler et al., *J. Clin. Chem. Clin. Biochem.*, vol. 28, pp. 129–138 (1990).

Various methods have been used to detect fructosamine, which is referred to herein as "protein-bound glucose" or "PBG." Use of the word "fructosamine" to refer to a protein-glucose Amadori rearrangement product is undesirable in part because it is not a recognized American Chemical Society or Chemical Abstracts protein chemical name or category and because it is also the trivial chemical name of a relatively simple compound unrelated to proteins or protein-sugar adducts. Hence the term "protein-bound glucose," which is more accurate and whose meaning is clear, is preferred and is used herein. Current procedures for measuring serum glycated proteins (i.e., protein-bound glucose) include affinity chromatography, agarose gel electrophoresis, high-performance liquid chromatography (HPLC), immunoassay with monoclonal or polyclonal antibodies, and colorimetric methods.

It was known that under the appropriate conditions, typically alkaline pH, certain compounds that were otherwise colorless in solution would be reduced by (that is, receive electrons from) the reducing sugar moiety of the protein-bound glucose and become colored. It was also known that the reaction conditions could be chosen so that the intensity of the color would be directly proportional to the concentration of protein-bound glucose in the sample being tested. For example, tetrazolium and other compounds have been used as color indicators. See, e.g., U.S. Pat. Nos. 3,576,815; 3,791,988; 4,642,295; 4,645,742; 4,956,301; Mattson et al., *Anal. Chem.*, vol. 22, no. 1, pp. 182–185 (January. 1950); Mopper et al., *Anal. Biochem.*, vol. 45, pp. 147–153 (1972); *Chem. Abstr.*, vol. 95, entry 148753e (Foods, 1981); Caines, *Clin. Biochem.*, vol. 19, pp. 26–30 (February 1986); Jue et al., *J. Biochem. Biophys. Meth.*, vol. 11, pp. 109–115 (1985); and *Chem. Abstr.*, vol. 82, entry 70120f (Biochem. Meth., 1975). An assay marketed by Roche Diagnostic Systems, Inc., Montclair, N.J., uses nitroblue tetrazolium ("NBT"). An assay marketed by Isolab Inc., Akron, Ohio, uses 2-(4-iodophenyl)-3-(4-nitrophenyl)-5-phenyltetrazolium chloride ("INT"). Trudinger, *Anal. Biochem.*, vol. 36, pp. 222–224 (1970), reports that methyl viologen is reduced by alkaline glucose to form a colored solution. Other compounds are known (including benzyl viologen) that change color and color intensity under the appropriate reaction conditions in the presence of reducing sugars or moieties of reducing sugars attached to proteins.

Johnson et al., *Clinica Chimica Acta*, vol. 127, pp. 87–95 (1982), report the advantages of measuring protein-bound glucose as an index of diabetic control. However, one recent review article concludes, based upon an analysis of literature articles concerning this type of test, that the test has not been evaluated sufficiently to allow its routine clinical use and that the results reported for it in the literature do not suggest that the test is reliable. See Windeler et al., *J. Clin. Chem. Clin. Biochem.*, vol. 28, pp. 129–138 (1990). The manufacturer of one commercial assay recently referred to the growing unease with the fructosamine assay, said that people are beginning to feel that the method has not lived up to its promise, and noted three technical problems with it. *Isolines*, vol. 19, no. 3, p. 1 (Isolab Inc., October 1990).

The literature also reports that various substances can interfere with assays (and particularly colorimetric assays) for protein-bound glucose, e.g., non-specific binding agents and, if elevated, uric acid and bilirubin. Interference is one of the three problems noted by Isolab (Id.). Elevated uric acid and/or bilirubin can be the result of disease or other process (e.g., liver disease, cancer). Approximately 1% of the general population and 6–7% of the hospital population have elevated levels. Colorimetric tests for protein-bound glucose in individuals having sufficiently elevated bilirubin and/or uric acid levels are viewed as unreliable and such tests are generally not run for those individuals.

U.S. Pat. Nos. 4,642,295 and 4,645,742, which use the coloring agent nitroblue tetrazolium ("NBT") under alkaline conditions to indicate the presence and concentration of protein-bound glucose ("PBG"), require that two colorimetric intensity readings be taken to try to reduce the adverse effects of certain interference. The first reading is taken after a suitable delay from the addition of NBT to the specimen (e.g., 10 minutes) to allow non-PBG/tetrazolium reactions to occur and the second reading is taken after a suitable delay following the first reading. If the first intensity reading is taken before substantially all of those non-specific (i.e., non-PBG) reactions have occurred, the difference in intensities between the two readings will include the intensity change caused by reaction of non-PBG compounds with the tetrazolium and that may introduce a significant error into the calculated PBG level. Because the NBT method uses two readings at different times following the addition of NBT to the specimen, it is also referred to as "the kinetic method." However, this method does not eliminate the adverse effects caused by elevated levels of uric acid and/or bilirubin.

It is known to add polyethylene glycol to serum to precipitate both glycated and non-glycated globulins while leaving glycated and non-glycated albumin and smaller molecules (e.g., uric acid and bilirubin) in solution, i.e., in the supernatant, and then to test the solution for glycated albumin by the nitroblue tetrazolium colorimetric method. That separation (precipitation) method leaves the non-protein, low molecular weight interfering substances in solution with the albumin, possibly to interfere with the colorimetric test if their levels are high enough. It is also known to use affinity chromatography on serum to separate glycated serum proteins (principally glycated albumin and glycated globulins) from the other substances present in the serum. These other substances do not bind to the column and include non-glycated proteins and the non-protein, low molecular weight interfering substances. The glycated proteins bound in the column are eluted and the protein concentration is measured by colorimetric or non-colorimetric methods. Mashiba et al., "Measurement of Glycated Albumin by the Nitroblue Tetrazolium Colorimetric Method," *Clinica Chimica Acta*, vol. 212, pp. 3–15 (1992). See also Armbruster, *Clin. Chem.*, vol. 33, no. 12, pp. 2153–2163 (1987). It is also known to add uricase to serum (to eliminate uric acid) along with the colorimetric reagent and then colorimetrically measure the glycated proteins in the serum.

Researchers disagree as to the effects of albumin on the NBT (nitroblue tetrazolium) test. Johnson et al., *Clinica Chimica Acta*, vol. 127, pp. 87–95 (1982), indicate that in the NBT test, correcting fructosamine for albumin concentration makes the difference between normal and diabetic sera less clear. On the other hand, Armbruster, *Clin. Chem.*, vol. 33, no. 12, pp. 2153–2163 (1987), a survey article, reports at pp. 2157–2158 conflicting opinions from other researchers. Some researchers said that hypoalbuminemia (clinically significant low albumin level) influenced the NBT assay only when the albumin concentration was less than 30–35 grams/liter. Other researchers found that protein-bound glucose values from the NBT method were affected by albumin regardless of the albumin concentration and they suggested a certain correction factor based on albumin concentration. Other researchers recommended a different correction based on albumin concentration. Yet other researchers did not find fructosamine to be significantly influenced by albumin concentration.

Rosenthal et al., *Clin. Chem.*, vol. 34, no. 2, pp. 360–363 (1988), report on a single-color-reading method for determining protein-bound glucose. At p. 362 they surmise that fructosamine concentrations from their method are affected by serum albumin concentrations in the same manner as the two-color-reading or kinetic method and that this should be taken into account for patients whose serum albumin concentrations are abnormal. Finally, Armbruster, *Clin. Lab. Sci.*, vol. 3, no. 3, pp. 184–188 (May/June 1990), another survey article, reports at p. 187 that the drawbacks of the NBT method include the nonspecific nature of the reaction in serum, the effects of albumin concentration, and how to best calibrate the test. Armbruster recommends that determining glycated hemoglobin instead of determining protein-bound glucose may be more advantageous when a patient's albumin or total protein values are low (Id.).

Thus, there are conflicting opinions in the literature as to whether detecting protein-bound glucose in serum is a reliable and accurate way to test for diabetes or to monitor the course of therapy, whether the presence of albumin significantly affects the NBT test for protein-bound glucose and if so, how to compensate for that effect, and whether an assay for determining protein-bound glucose should be used at all for patients who have low albumin levels.

Furthermore, no reliable method exists for eliminating or significantly reducing the adverse effects of, e.g., elevated uric acid and/or bilirubin levels in PBG assays, particularly colorimetric assays. Accordingly, there is a continuing need for a reliable, reproducible, relatively rapid, and relatively inexpensive method for testing individuals for diabetes with high accuracy and for monitoring the course of diabetes therapy, even if those individuals have levels of uric acid, bilirubin, and/or other substances that would otherwise interfere with determination of their protein-bound glucose.

SUMMARY OF THE INVENTION

A method of testing individuals for diabetes that satisfies those requirements has now been developed. Other features and advantages of the method of this invention will be apparent to those skilled in the art from this disclosure.

One aspect of the invention concerns a method of reducing interference from interfering substances in an assay for the presence of protein-bound glucose, said method comprising treating a composition containing interfering substances and protein-bound glucose comprising glycated albumin and other glycated proteins to produce a product to be used in the assay that as compared to the composition is substantially richer in glycated albumin and substantially poorer in interfering substances.

Another aspect of the invention concerns a method of determining protein-bound glucose that is principally glycated albumin, said method comprising:

(a) treating a composition containing protein-bound glucose and interfering substances comprising uric acid, bilirubin, glutathione, and ascorbic acid and its metabolites to produce a product that is substantially free of those interfering substances; and (b) colorimetrically assaying the product for protein-bound glucose.

Another aspect of the invention concerns a method of reducing interference from interfering substances in an assay for the presence of protein-bound glucose, said method comprising contacting a composition containing protein-bound glucose and one or more interfering substances with a reagent to produce a precipitate to be used in the assay that comprises protein-bound glucose that can be redissolved and that is substantially free of one or more of the interfering substances.

Another aspect of the invention concerns a method of assessing the likelihood of an individual in a population having diabetes even if specimens from the individual used for such assessment contain interfering substances that would otherwise tend to interfere with such assessment, said method including the steps:

(a) obtaining from the individual a specimen that contains protein-bound glucose that is principally glycated albumin and which may contain one or more interfering substances that may interfere with a subsequent assay for protein-bound glucose;

(b) treating the specimen to produce a product that as compared to the specimen is substantially richer in protein-bound glucose and substantially poorer in one or more of the interfering substances;

(c) treating the product from step (b) to determine the level of protein-bound glucose for the individual;

(d) determining the glucose level for that individual; and (e) comparing the levels of protein-bound glucose and glucose for the individual to pre-established values that together tend to indicate whether an individual is likely to have diabetes.

Another aspect of the invention concerns a method of assessing the likelihood of an individual in a population having diabetes even if specimens from the individual used for such assessment contain interfering substances that would otherwise tend to interfere with such assessment and in which the population has been divided into different categories based on their glucose levels and protein-bound glucose levels, some of which categories are associated with a greater or a lesser likelihood of having diabetes, said method including the steps:

(a) obtaining from the individual a specimen that contains protein-bound glucose that is principally glycated albumin and which may contain one or more interfering substances that may interfere with a subsequent assay for protein-bound glucose;

(b) treating the specimen to produce a product that as compared to the specimen is substantially richer in glycated albumin and substantially poorer in one or more of the interfering substances;

(c) treating the product from step (b) to determine the level of protein-bound glucose for the individual;

(d) determining the glucose level for that individual; and (e) comparing the levels of protein-bound glucose and glucose for the individual to pre-established values that together place the individual into one of the categories.

In a preferred aspect of the invention, the specimen from the individual whose diabetic status is being determined is treated, preferably with a precipitating agent (e.g., uranyl acetate) to precipitate the glycated albumin, which typically accounts for about 80% of the protein-bound glucose in the specimen. The supernatant will contain substantially all of the interfering substances that were present in the specimen, and the precipitate, which is substantially free of the interfering substances, will then be assayed for protein-bound glucose. "Substantially free of interfering substances" means that the level of interfering substances in a material to be assayed is low enough so that those substances do not cause any clinically significant error in the assay for protein-bound glucose. The clinical variables used herein (glucose, protein-bound glucose, and optionally albumin) are preferably determined from blood serum (referred to herein as "serum"). Under appropriate conditions other blood derivatives may also be tested to determine one or more of those three values. In another preferred aspect of the invention, the protein-bound glucose is determined by a colorimetric method, preferably using an electron acceptor, which most preferably is a viologen such as benzyl viologen or methyl viologen.

Applicants believe that the evidence is not conclusive yet regarding whether normalization is necessary or desirable if the individual in question has hypoalbuminemia. Thus, the method of this invention allows the value for protein-bound glucose to be used as such or to be normalized, e.g., to account for individuals having hypoalbuminemia. One method of determining normalized protein-bound glucose for an individual is to determine the protein-bound glucose level, determine the albumin level, and divide the protein-bound glucose level by the albumin level to yield the individual's normalized protein-bound glucose level ("normalization"). The method of assessing the risk of having diabetes will then use the individual's glucose value and either his or her protein-bound glucose value or his or her normalized protein-bound glucose value.

The method of this invention can be used to preliminarily screen people for diabetes or it can be used as a secondary test. Advantages of the invention include the increased sensitivity and accuracy of the method, e.g., for detecting individuals who have diabetes but who have unusually low albumin levels and, thus, might be reported as normal in a standard NBT test for protein-bound glucose; for discriminating between non-fasting subjects who have and who do not have diabetes, all of whom might be reported as probable diabetics from the standard glucose test; for detecting specimens that may have been mishandled; and for more accurately determining the PBG level for an individual even if that individual (and thus a specimen taken from that individual) has sufficiently high levels of interfering substances. For example, elevated uric acid and/or bilirubin may cause erroneously high PBG, which in turn increases the likelihood that the patient will be erroneously reported to be diabetic. Increased accuracy in detecting whether a patient has diabetes obviously reduces the number of follow-up tests (and associated cost and time) that would otherwise be necessary and allows any necessary therapy to begin sooner.

The method of this invention for reducing the effect of interfering substances finds particular use when protein-bound glucose is to be determined by a colorimetric assay. In a colorimetric assay used in this invention, interfering substances are non-protein, low-molecular weight substances that could interfere with the colorimetric determination of PBG and that are typically endogenous (but could also be exogenous) and are typically reducing substances, for example, uric acid, bilirubin, glutathione, ascorbic acid and its metabolites, and certain drugs (e.g., quinones). Thus, preferably, the non-protein, low molecular weight substances that are substantially eliminated by the method of this invention from the composition or specimen to be further tested are selected from the group consisting of uric acid, bilirubin, glutathione, and ascorbic acid and its metabolites. Also preferably, the method of this invention removes a substantial portion of each of those substances (uric acid, bilirubin, glutathione, and ascorbic acid and its metabolites) from the composition or specimen to be further tested for glycated protein, i.e., the composition or specimen is substantially free of each of those substances. By "substantially free" is meant that at least 70%, desirably at least 80%, preferably at least 90%, more preferably at least 95%, and most preferably at least 98% of the interfering substances that are in the composition or specimen to be treated are not found in the product or precipitate after the treatment. Thus, most preferably, at least 70%, desirably at least 80%, preferably at least 90%, more preferably at least 95%, and most preferably at least 98% of each of the interfering substances selected from the group consisting of uric acid, bilirubin, glutathione, and ascorbic acid and its metabolites that are in the composition or specimen to be treated are not found in the product or precipitate after the treatment.

Typically the glycated albumin is at least 50%, desirably at least 60%, preferably at least 70%, and more preferably about 80% of the protein-bound glucose. "Product to be used in the assay" and "assaying the product" refer to the fact that the product is used in the assay for protein-bound glucose as is or after further treatment. For example, if treating the composition results in a "product" that is a precipitate, it may be necessary to redissolve the precipitate (after it has been separated from the supernatant, which contains interfering substances) so that the subsequent assay for the protein-bound glucose, e.g., a colorimetric assay, can be performed (because colorimetric assays typically are performed on liquids and not solids). "Precipitate to be used in the assay" refers to the fact that the precipitate is used as is or after further treatment.

Usually at least 70%, desirably at least 80%, preferably at least 90%, more preferably at least 95%, and most preferably at least 98% of the glycated albumin that is in the composition or specimen to be treated is found in the product or precipitate after the treatment. Usually at least 70%, desirably at least 80%, preferably at least 90%, more preferably at least 95%, and most preferably at least 98% of the interfering substances that are in the composition or specimen to be treated are not found in the product or precipitate after the treatment. Use of uranyl acetate as the precipitating agent usually results in obtaining the higher values for each of those ranges, i.e., with uranyl acetate the amount of glycated albumin in the composition or specimen that is found in the product or precipitate after treatment is usually closer to the 98% value than to the 70% value, and the amount of interfering substances not found in the product or precipitate is usually closer to the 98% value than to the 70% value.

BRIEF DESCRIPTION OF THE DRAWING

To facilitate further description of the invention, the accompanying figure is provided. The ordinate shows PBG level (in milligrams of protein-bound glucose in serum per deciliter of serum) for individuals in a population and the abscissa shows their respective glucose level (in milligrams of glucose per deciliter of serum). Thus, the point on this graph for an individual will be determined by the individual's PBG and glucose values. The plot has been divided into six regions or categories, indicated by I, II, III, IV, V, and VI. The significance of each category is described below. It should be understood that the drawing is provided for descriptive purposes and should not be construed to unduly limit the scope of the claims.

DETAILED DESCRIPTION OF THE INVENTION

Any clinically acceptable assay for glucose and protein-bound glucose (and albumin, if determined and used to normalize the value for protein-bound glucose) may be used. However, the method of this invention for reducing the effect of interfering substances finds particular use when protein-bound glucose is to be determined by a colorimetric assay. In a colorimetric assay used in this invention, interfering substances are typically endogenous low-molecular weight reducing substances that could interfere with the colorimetric determination of PBG, for example, uric acid, bilirubin, glutathione, ascorbic acid and its metabolites, and certain drugs (e.g., quinones).

Desirably, the blood derivative on which the assays are performed is serum. Assays for determining glucose, protein-bound glucose, and albumin in the serum of an individual are well-known. When using the preferred method of reducing the effect of interfering substances in the PBG assay, that is, to use uranyl acetate as a precipitating agent to precipitate PBG and leave one or more of the interfering substances in the supernatant, the specimen for the PBG assay will preferably be serum that is not hemolyzed or lipemic. Desirably, a colorimetric test is used for determining protein-bound glucose ("PBG"), which test may be automated and run at the same time the glucose and albumin tests are run. Desirably, all tests are automated and all are run with substantially the same equipment, desirably a multi-channel instrument. A single specimen may be used and subdivided for the various tests. After uranyl acetate or other precipitating agent has been added to a specimen, glucose and albumin assays desirably are not run on that specimen or on the resulting supernatant.

The protein-bound glucose test used to determine PBG desirably is an automated colorimetric in vitro assay for quantifying the amount of glucose covalently linked to the lysine and terminal amino groups of various serum protein, the principal one of which is albumin. The attachment of glucose to the amino groups of proteins is a non-enzymatic, post-translational process often referred to in modern technical literature as "protein glycation."

As explained above, circulating plasma proteins may become non-enzymatically glycated in the same manner as the hemoglobin of red blood cells. Glycation is a slow, continuous, and irreversible reaction whose rate and extent depend principally on the glucose concentration to which the proteins are exposed. When serum proteins are glycated in vivo, glycated albumin usually accounts for about 80 percent of the glycated serum proteins (that is, protein-bound glucose). See, e.g., Dolhofer et al., *Clinica Chimica Acta*, vol. 112, pp. 197–204 (1981); U.S. Pat. No. 4,956,301, column 10, line 8 et seq. Just as with glycohemoglobin (glycated hemoglobin), the amount of protein-bound glucose increases in patients with poorly controlled diabetes.

A number of studies have documented that protein-bound glucose levels can be elevated despite seemingly normal levels of glycohemoglobin. That is consistent with the fact that the half-life of albumin and, therefore, of glycated albumin is shorter, about 19 days, whereas the half-life of hemoglobin and, therefore, of glycated hemoglobin is about 60 days. Accordingly, a patient's glycated hemoglobin level, which indicates long-term glycemia, may be normal whereas the protein-bound glucose level, which indicates intermediate-term glycemia, may be elevated. Thus, determining protein-bound glucose may provide an early warning of the onset of diabetes or an indication of transient hyperglycemia, which may not be revealed by subsequent glycohemoglobin assay.

In the method of this invention, the normalized PBG level of the individual may be used, although normalization may not be necessary, even for individuals who have hypoalbuminemia. Any method of normalization can be used provided it allows for and facilitates detecting the existence of diabetes in a patient using the method of this invention even if the patient also has hypoalbuminemia. Normalization is preferably accomplished by dividing the assay value for PBG level by the assay value for albumin level. Another method of normalizing is dividing the raw PBG level by a factor proportional to the albumin level, for example, dividing the PBG level by half of the albumin level. Another method is to categorize individuals based on their albumin levels, assign a different factor to each albumin level, and multiply or divide the raw PBG level for an individual by the factor for that individual corresponding to that individual's albumin level.

The chemistry of glycation and of the preferred PBG assay are further described as follows. In the first step of glycation, the carbonyl group of glucose combines with the amino groups of proteins to form aldimine (1-amino-1-deoxyglucose) intermediates known as Schiff bases. In the second step, the labile aldimine-Schiff base intermediates undergo the Amadori rearrangement (the isomerization of aldosylamine to a 1-amino-1-deoxyketose) to yield a relatively stable ketoamine adduct to the protein. The straight-chain ketoamine adduct is thought to undergo cyclization to a more stable hemiketal furanose or pyranose ring structure.

Ketoamine-linked N-(1-deoxyfructos-1-yl) groups, the Amadori rearrangement products when the Schiff base originates from glucose, are electron donors (reducing substance) at alkaline pH levels. The reducing power of these Amadori rearrangement products in dilute NaOH at room temperature has been demonstrated by the conversion of o-dinitrobenzene to a purple color after one minute; by rapidly decolorizing methylene blue and dichlorophenolindophenol; and by reduction of Fehling solution, Tollen's reagent, nitroblue tetrazolium, and other tetrazolium salts.

The preferred PBG assay is based on the ability of Amadori rearrangement products to transfer electrons under alkaline conditions, in the presence or absence of oxygen, to a colorimetric reagent, which is a mixture of colorless, low-potential redox indicators widely used as artificial electron carriers in enzymic systems. The electron acceptor reagent preferably used herein comprises 1,1'-dibenzyl-4,4'-bipyridinium dichloride (benzyl viologen); 1,1'-dimethyl-4,4'-bipyridinium dichloride (methyl viologen); and heterocyclic azole compounds as chromaphoric stabilizers. The transfer of electrons to the reagent results in the formation of blue, stable, free-radical cations (wavelength of maximum absorbance is 540 nanometers). The absorbancy of the solution containing the blue-colored reduced compounds is proportional to the amount of protein-bound glucose in the patient's sample.

The reagent typically will be stored as a dry powder. When reconstituted with deionized water, the aqueous reagent solution preferably used in this assay will contain 212 milligrams per liter of the above-described electron acceptor reagent in a molar ratio of 1 part of benzyl viologen, 1 part of methyl viologen, and 0.1 part of chromaphoric stabilizer. A tetrazolium compound may be used as the stabilizer and preferably triphenyl tetrazolium chloride is used.

As used in the preferred PBG assay, the aqueous solution of electron acceptor reagent also contains 10.4 grams/liter of sodium carbonate and 5.5 grams/liter of sodium bicarbonate. With these quantities, the pH of the reagent solution is 10.5 and the pH of the reaction mixture (specimen plus reagent solution) is 10.5. The pH of the solution may be increased or decreased by increasing or decreasing the quantities of carbonate and bicarbonate used. It has been found that the pH of the reaction mixture should be at least about 10.0 so that the reduction of the electron acceptor compounds (the viologens) will proceed sufficiently rapidly. However, if the pH is too high, other compounds (for example, glucose) in the specimen will also react with the electron acceptor compounds to produce a greater intensity of color than is otherwise due to the PBG. This interference becomes noticeable when using NBT as the coloring agent if the pH is higher than about 10.8. With the preferred electron acceptor reagent described above, such interference by glucose, for example, is not significant until the pH is greater than about 12.6. Accordingly, because any acceptable coloring agent may be used in a colorimetric method for detecting PBG, one skilled in the art will know that the pH of the aqueous coloring agent should be adjusted so that it is sufficiently alkaline for the reaction to proceed satisfactorily but not so alkaline that interference by glucose or other compounds present in the specimen that have not been eliminated by the previous separation (e.g., precipitation) becomes significant.

The aqueous reagent solution described above should be stored in a dark bottle and held at 2°–8° C. Under those conditions, the aqueous reagent solution will be stable for at least five days and possibly for up to 30 days. The preferred dry reagent described above is available for determining PBG from National Screening Institute of Metuchen, N.J.

The preferred PBG assay used in the method of this invention is run at 37° C. and preferably is carried out automatically on a serum specimen using either a Hitachi 736–50 Analyzer or an Olympus AU5000 Analyzer. The following operating parameters have been found to be satisfactory for each of the two analyzers:

| Hitachi 736-50 Analyzer Instrument Parameters | |
|---|---|
| Channel No.: | # PBG |
| Assay Code: | ENDPOINT-20-20 |
| Sample Volume: | 15 |
| R1 Volume: | 250–9999 |
| R2 Volume: | 0–9999 |
| Wavelength 1: | 700 NM |
| Wavelength 2: | 546 NM |
| Reagent Blank Absorption: | −1–0 |
| Reagent Blank Concentration: | 0 |
| Standard Concentration: | Use Assayed Value Of Bovine Serum Calibrator |
| Recalibrate (Blank): | 1 |
| Recalibrate (Standard): | 3 |
| Factor: | 4267 |
| Unit Factor: | 1.00 |
| Standard Absorption: | 10% |
| Allowance | |
| Normal Range Low: | 0 |
| Normal Range High: | 9999 |
| Absorption Limit (Rate): | 0 (Increase) |
| Olympus AU5000 Analyzer Instrument Parameters | |
| Operation: | Yes |
| Sample Volume: | 15 microliters |
| Reagent Volume | |
| R1: | 250 microliters |
| R2: | 0 |
| W3 Operation | |
| R1: | Yes |
| R2: | No |
| Method: | End |
| Wavelength 1: | 540 |
| Wavelength 2: | 750 |
| Reaction Slope: | + |
| Measuring Point | |
| Start: | 8 |
| End: | 8 |
| OD Value Range | |
| Max.: | N/A |
| Min.: | N/A |
| Limit Of Linearity: | N/A |
| Repeat Range | |
| High: | |
| Low: | |
| QC Group | |
| 1: | 1 |
| 2: | 2 |
| Reagent OD Range | |
| Max.: | 2.000 |
| Min.: | −0.1000 |

Usually only one intensity measurement is needed with the preferred PBG assay because desirably the interfering substances have been substantially removed from the product or precipitate on which the PBG assay is run. Alternatively, two, three, or more intensity readings may be utilized. However, more than two measurements may unduly increase the total time required for running a PBG assay. Generally, the time for taking a single reading will be 5–20 minutes, desirably 5–15 minutes, and preferably eight minutes after the reagent solution and treated specimen (desirably the redissolved precipitate from the precipitation step) are combined to form the reaction mixture. When using automated equipment such as the above-described Hitachi and Olympus analyzers, eight minutes is the preferred time for a single reading or for the last reading when two or more readings are used. That is because eight minutes is the maximum set time for those machines. The optimum times for taking the reading(s) for a particular PBG colorimetric assay with particular equipment can readily be determined. As will be understood by one skilled in the art, the times will be affected by which colorimetric reagent is used, its concentration in the reaction mixture, the pH and temperature of the reaction mixture, and the equipment employed.

For quality control of the PBG assay, control sera from National Screening Institute are preferred. MAS Control I and MAS Control III, available from Medical Analysis Systems Inc. of Camarillo, Calif., may also be used. Any other satisfactory control sera may be used. The MAS controls are liquid human sera and should be stored according to the manufacturer's recommendations. In one study, MAS Control I produced a mean value of 3.91 milligrams of PBG per deciliter of serum (with a range of 3.76–4.12 mg/dl) and MAS Control III yielded a mean value of 6.55 milligrams PBG/deciliter of serum (with a range of 6.38–6.72 mg/dl).

Use of commercially available control sera may result in unusually high PBG values, for the following reason. In making control sera, manufacturers usually pool large amounts of sera and allow the sera to sit for extended periods of time. During these lengthy periods, the glucose in the sera continuously reacts with the serum proteins. Thus, these control sera may have abnormally high PBG levels. Although it is difficult and expensive to prepare serum controls that have not suffered such glycation, the control sera from National Screening Institute yield normal PBG values. Such sera are produced by collecting fresh serum from non-diabetics, dialyzing the serum to remove endogenous glucose, and lyopholizing the serum. Obviously, control sera that give normal PBG values are preferred and can be prepared by anyone skilled in the art.

It has also been found that hemolysis interferes with the preferred PBG assay and, therefore, the preferred method of this invention should not be performed using hemolyzed serum or with lipemic serum.

With respect to calibration standards for the preferred PBG assay, samples of bovine calibrator are available from National Screening Institute, which assigns a calibration value (milligrams of PBG per deciliter of reconstituted calibrator). National Screening Institute obtains the calibrator from the Gilford division of Ciba-Corning Diagnostics, Oberlin, Ohio. Gilford Calibrator Catalog No. 606-871-2 has been found to be satisfactory. The HPLC method of Schleicher et al., *J. Clin. Chem. Clin. Biochem.*, vol. 19, pp. 81–87 (1981), has been found to be satisfactory for assigning a calibration value to the Gilford bovine calibrator. Other suitable calibration standards and methods may be used. It has been found that the Gilford calibrator should be stored under refrigeration (for example, at 2°–8° C.) until its expiration date. The calibrator may be reconstituted with the ionized water and mixed gently, for example, for 30 minutes. The reconstituted calibrator if stored properly (for example, at 2°–4° C.) is stable for 24 hours.

In a study of about 2,600 patients using the Hitachi 736-50 and Olympus AU5000 analyzers, the normalized PBG reference range was found to be less than 1.20 milligrams PBG per gram of albumin. Thus, for the patient population surveyed the cut-point for the upper limit of normal for the ratio of protein-bound glucose to albumin (that is, normalized protein-bound glucose) was found to be 1.2 milligrams PBG/grams albumin. In interpreting the results of the preferred PBG assay, specimens whose normalized PBG levels are less than 0.3 mg PBG/g albumin or greater than 4.0 mg PBG/g albumin should be retested. That study was performed on specimens that were not subjected to the separation step to eliminate interfering substances prior to the PBG colorimetric assay.

It has been found for the preferred colorimetric PBG assay using the preferred colorimetric reagent that uric acid levels equal to or above 8.5 milligrams/deciliter cause the PBG values determined by that assay to be higher than the true value by 10% or more and that bilirubin levels equal to or above 2.0 milligrams/deciliter also cause a 10% or greater error. Despite the general practice of not using colorimetric methods to determine PBG if the patient has elevated uric acid and/or bilirubin levels, it has been found that PBG level can successfully be used as one of the two key indicators in the method of this invention (in addition to the glucose level) provided it is determined from a specimen that has been treated using the separation step of this invention. The thus-obtained PBG value and the glucose value (the other key indicator) are utilized together to place the individual into one of several categories that have been previously established for the population and against which the individual is to be compared.

Figure 1:
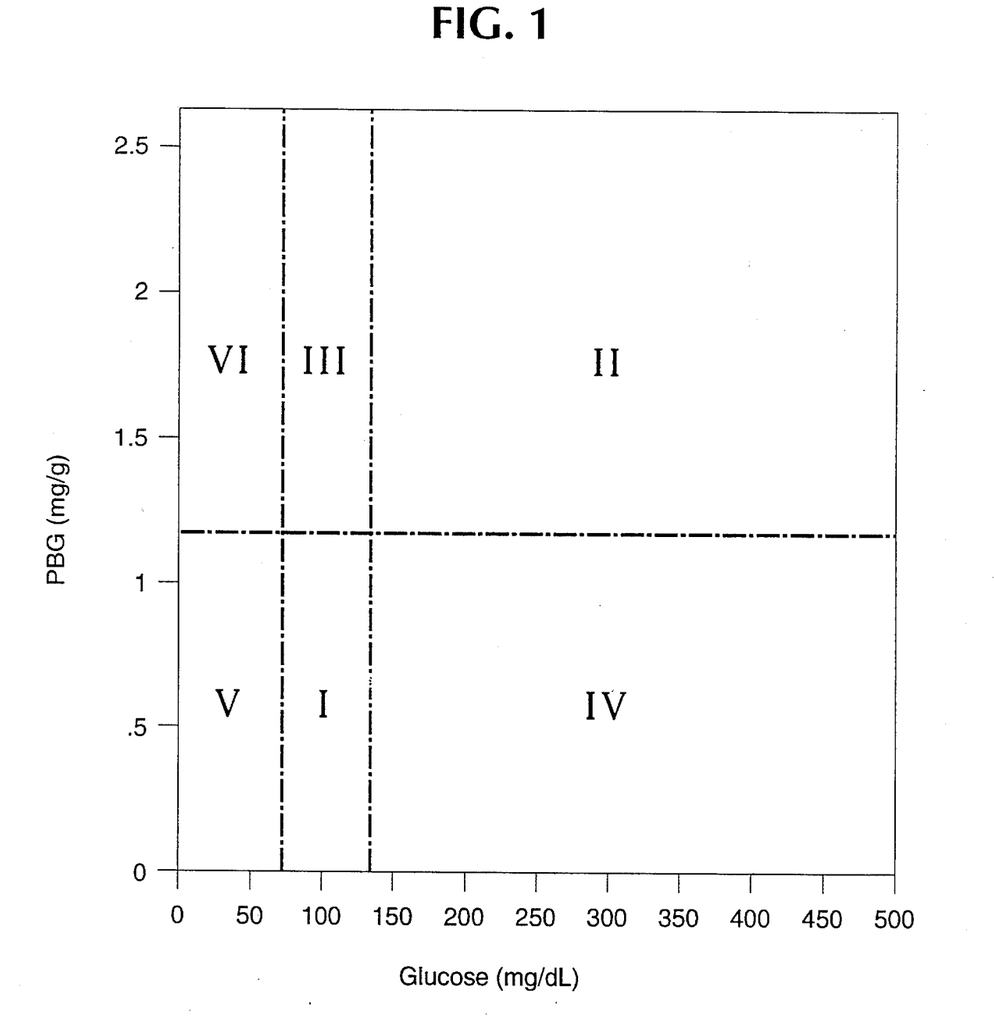

Using the combination of serum glucose and serum PBG (optionally normalized) obtained in accordance with this invention is superior to using glucose alone or PBG (or normalized PBG) alone in testing for diabetes. The combination allows a physician to determine whether a serum glucose result is representative of glycemia over the previous 1–2 weeks, better interpret the glycemic status of non-fasting subjects (because PBG is an integrated measure of the average level of glycemia over the previous two weeks or so), and determine that significant periods of hyperglycemia have been present in diabetic patients who may present normal serum glucose. Eliminating interfering substances prior to assaying for PBG allows a more accurate PBG value to be obtained and used in conjunction with glucose level, with concomitant increase in the accuracy of diagnosis or assessment. Other advantages of using the combination will be apparent from further consideration of the figure.

The PBG/glucose plot of the accompanying figure is divided into six sections or categories. The dark vertical line separating sections I and III from sections V and VI is drawn at the cut-point for the population surveyed for the lower limit of normal for glucose level, which in this case is established at about 65 milligrams of glucose per deciliter of serum. The dark vertical line separating sections I and III from sections II and IV is drawn at the cut-point for the population for the upper limit of normal for glucose level, which in this case is established at about 130 milligrams of glucose per deciliter of serum. The dark horizontal line separating sections I, IV, and V from sections II, III, and VI is drawn at the cut-point for the population for the upper limit of normal for the ratio of protein-bound glucose to albumin (normalized PBG), which in this case is established at about 1.2 milligrams of PBG per gram of albumin.

Obviously the values at which the cut-points are established will vary, depending on a number of factors, including which assays are used, the calibration and standardization values, the equipment used, the units in which the glucose and normalized PBG levels are expressed, and, if used, the method employed to normalize the PBG level for albumin level. The cut-points may also vary depending upon the genetic background of the population surveyed and their diets. Other factors may also affect the cut-points established, such as what a clinician considers "normal" for glucose level and PBG level. Establishing a cut-point for the upper limit of normal for the PBG value is well within the skill of the art as are establishing the cut-points for the upper and lower limits of normal for glucose level.

After the figure or equivalent (e.g., computer database) is prepared for the reference population, it can then be used as the basis for making an assessment of the likelihood that a patient has diabetes. A patient whose glucose value and PBG value place him or her within category I probably does not have diabetes (or if he or she is a known diabetic, the course of therapy is being successful) because the glucose and PBG levels are consistent with normoglycemia (normal glycemia). A patient whose glucose and PBG level place him or her in region II of the figure has a higher than average probability of having diabetes because his or her glucose and PBG levels are consistent with clinically significant hyperglycemia. The patient should be retested with a standard confirmatory test.

A patient whose glucose and PBG levels place him or her within section III of the figure has normal glucose but elevated PBG and may be diabetic. A glucose test alone would not reveal the possible diabetes.

A patient whose glucose and PBG levels place him or her in category IV have elevated glucose levels but normal PBG levels. That indicates transient hyperglycemia. Such a patient was probably normoglycemic over the past two weeks. The elevated glucose level may indicate the contemporaneous onset of diabetes or that the patient did not fast for a sufficiently long time before his or her blood specimen was taken or that he or she has recently been on low-carbohydrate diets. For such patients the standard glucose test alone would indicate the need for further testing, which might unduly worry them. However, because both glucose and PBG levels are determined and because the PBG levels are not above the established cut-point, a physician may advise patients who appear to belong in category IV that they probably do not have diabetes and/or make further inquiry concerning their diet and whether they fasted before the blood sample was taken.

A patient placed in category V exhibits low glucose level and normal PBG level. This suggests hypoglycemia or possible specimen mishandling. Specimens from such patients may have individuals may have suffered in vitro glycolysis because, as discussed above, the glycation reaction between blood proteins and glucose proceeds continuously. If a specimen is inadvertently allowed to stand too long before being assayed, the glucose level will fall.

A patient placed in category VI exhibits low glucose level and elevated PBG level. That suggests possible hypoglycemia or possible mishandling of the specimen. As explained, if sufficient time elapses before a specimen is analyzed, the glucose level may fall significantly and the PBG level may rise significantly as glycation occurs. If such a delay in processing the specimen has not occurred, the results suggest that the patient may have had significant hyperglycemia during the previous two weeks. A patient assigned to category V or VI probably should be retested within a week or two.

Patients who have sufficiently elevated uric acid and/or bilirubin to result in erroneously high PBG values if the separation step of this invention were not employed might as a result be placed in category II; however, the method of this invention tends to eliminate such interfering substances prior to the PBG assay and thereby tends to result in those patients being correctly placed instead in category IV, thereby resulting in a change of diagnosis.

It is not necessary that the reference population be divided into six categories; a greater or lesser number of categories may be used depending on how many cut-points are established. For example, a cut-point for the lower limit of normal for the glucose level need not be established or utilized.

In the preferred separation of this invention for reducing the effect of interfering substances on the subsequent PBG assay, preferably a precipitating agent is used, most preferably uranyl acetate. Thus, the specimen, preferably serum, is combined with the precipitating agent. The resulting precipitate is separated from the supernatant, the precipitate is redissolved, and the assay (preferably colorimetric), is run on the resulting solution.

The precipitate will contain glycated protein (PBG) that is substantially glycated albumin. The supernatant will contain substantially all of the interfering substances. It is important that the precipitating agent not denature the protein of the precipitate (principally albumin) otherwise it will be difficult or impossible to redissolve the precipitate to obtain a solution of glycated protein on which to run the PBG assay.

Uranyl acetate is the preferred precipitating agent. It breaks ionic bonds between albumin and other substances (e.g., the interfering substances), does not break covalent bonds between albumin and other substances (e.g., the sugar-albumin bonds of the glycated albumin), and precipitates the glycated albumin without denaturing the albumin, thereby permitting dissolution of the precipitate for the PBG assay, which is desirably a colorimetric assay.

The preferred precipitating agent is preferably used as an aqueous solution in which 600 microliters of solution contain 4.1 millimoles/l of uranyl acetate. The solution is buffered to a pH of 4.1 using sodium acetate buffer and it contains 1% by volume of methanol as a stabilizer.

Albumin accounts for about 80 percent of the glycated proteins in the serum of almost all people. Thus, separating glycated albumin from the other glycated proteins in the specimen (e.g., glycated globulins) does not affect the validity of using the PBG value obtained on material resulting from the separation step of this invention instead of using a PBG value that would otherwise be obtained on the specimen without any separation step. Furthermore, as explained above, without the separation step of this invention, interfering substances would tend to result in erroneous PBG values.

The use of the method of this invention is illustrated as follows. Forty-five microliters each of calibrator, controls I and II, and patient samples are pipetted in polypropylene microcentrifuge tubes. Six hundred microliters of the preferred precipitating agent solution are added to each tube, the tubes are capped, and the contents are mixed by a vortex mixer. The capped tubes are placed in a microcentrifuge (e.g., HERMLE model BHG) and are centrifuged at 15,000 rpm for 3 minutes at room temperature. The contents are decanted and the supernatant is discarded by inverting the tubes and tapping the open ends a few times to remove any trace of supernatant. To the remaining precipitate in each tube is added 1.5 milliliters of the preferred colorimetric indicator described above. The tubes are capped and placed in a heating block held at 37° C. After 15 minutes, the tubes are mixed one at a time by vortex mixing after which mixing each tube is immediately returned to the heating block. It is important that the precipitate in each tube be completely redissolved. At the end of 30 minutes total for each tube, each tube is removed from the heating block and the contents are mixed by inverting the tube three times. Using a spectrophotometer that has been "zeroed" against water, the absorbance of the contents of each of the tubes is measured at 538 nanometers after the contents has been transferred to an appropriate cuvette.

The data are then manipulated as illustrated by the following to determine the PBG values for the unknowns. Assume that the absorbance of the calibrator has been determined to be 0.181, that of control I (non-diabetic) to be 0.155, and that of control II (diabetic) to be 0.327. The PBG value for control II is thus 0.327/0.181, which equals 1.81. The PBG value for patient 1, who had an absorbance reading of 0.186 is 0.186/0.181, which equals 1.03, and the PBG value for patient 2, who had an absorbance reading of 0.288 is 0.288/0.181, which equals 1.59. The PBG values for patients 1 and 2 in combination with their individual glucose values will allow an assessment to be made as to the likelihood of each of them having diabetes, for example, by placing each of them into one of the six categories shown in the figure.

PBG values for 191 patients obtained using the method of this invention (with the separation step) were compared to their Hemoglobin A1c values obtained using the commercially available Biorad Diamat System Analyzer. The overall coefficient of correlation (r) between the thus-determined PBG and Hemoglobin A1c values for the 191 patients was found to be 0.91, which is excellent correlation.

As will be obvious to one skilled in the art, use of PBG obtained using the separation method of this invention and glucose together to characterize the patient's biochemistry for assessment significantly enhances a physician's picture of the patient regarding possible diabetes and allows the physician to provide additional information to the patient. For example, for patients whose glucose levels and PBG levels place them in category IV, a physician can ask them to be retested without alarming them by telling them that they probably do not have diabetes but that for some reason the glucose levels were unusually high. Without knowing he or she displayed a normal PBG value, an individual who had a glucose level over 200 mg/dl might be unduly alarmed if asked to submit to further testing. Similarly, an individual whose glucose level appeared to be normal, for example, slightly over 100 mg/dl, would not be detected as probably having diabetes and therefore needing further testing if his or her PBG value of just over 2.0 were not also provided to the physician. If that individual also suffered from hypoalbuminemia, the PBG value might or might not place the individual under the cut-point of the upper limit of normal for PBG values (i.e., in category I) whereas normalization might obviate that problem.

Variations and modifications in this invention will be apparent to those skilled in the art and the claims are intended to cover all such variations and modifications that fall within the true spirit and scope of the invention. For example, it is not necessary that graphical methods be used with the PBG (optionally normalized) and glucose levels to divide the reference population into categories. Any method can be used for such categorization and the different categories or groupings need not even be called "categories" or the like. What is common about all of the methods that can be used is that combinations of the two variables (glucose and PBG) for an individual being tested when compared to the appropriate reference values for the reference population allow that individual's probable risk of having diabetes to be assessed. Thus, for example, cut-points for the reference population can be established within the ranges of values for PBG level (optionally normalized) and glucose level, and the cut-points can be chosen so that values above or below the cut-points have some clinical significance to facilitate such assessment.

It should be understood that these cut-points for "normal" may not strictly correspond to what physicians would in the abstract consider normal. For example, a cut-point may be chosen to err on the side of safety so that those who would otherwise be classified as borderline but still "normal" are identified as possibly needing further testing.

It should also be understood that the reference population cut-points for any one of the variables may vary with the values for the other variables, e.g., the upper limit of normal for glucose may vary with the PBG level. In graphical terms, with reference to the figure, that would mean, for example, that the straight vertical line separating regions I and III from regions II and IV might instead be established as a curved line, or a diagonal straight line, or a partially vertical/ partially curved or diagonal line, or a combination thereof, and the same is true for any of the other cut-points.

We claim:

1. A method of determining protein-bound glucose in a specimen composition containing protein-bound glucose and one or more interfering substances that may interfere with an assay for protein-bound glucose, said method comprising the steps:

(a) contacting at a pH of about 4.1 the specimen composition with a first reagent composition containing about 4.1 millimoles/liter of uranyl acetate to precipitate protein-bound glucose without denaturing it to produce (i) a precipitate product comprising protein-bound glucose that can be redissolved and that is substantially free of the one or more interfering substances and (ii) a supernatant containing the one or more interfering substances;

(b) separating the precipitate product from the supernatant;

(c) dissolving the precipitate product to give a solution of redissolved protein-bound glucose that is substantially free of the one or more interfering substances; and (d) contacting the redissolved protein-bound glucose in solution at a pH of at least about 10.0 with a colorimetric reagent that colorimetrically indicates the presence of protein-bound glucose.

2. The method of claim 1 wherein the one or more interfering substances are selected from the group consisting of uric acid, bilirubin, glutathione, ascorbic acid, and its metabolites.

3. The method of claim 1 wherein the protein-bound glucose is principally glycated albumin.

4. The method of claim 1 wherein the colorimetric reagent comprises an electron acceptor.

5. The method of claim 4 wherein the electron acceptor is selected from the group consisting of benzyl viologen and methyl viologen.

6. The method of claim 4 wherein the colorimetric reagent comprises benzyl viologen and methyl viologen.

7. The method of claim 1 wherein step (a) is conducted at room temperature.

8. The method of claim 1 wherein step (c) is carried out at about 37° C.

9. The method of claim 1 wherein steps (c) and (d) are performed simultaneously.

10. A method of determining protein-bound glucose in a specimen composition containing protein-bound glucose and one or more interfering substances selected from the group consisting of uric acid, bilirubin, glutathione, ascorbic acid, and its metabolites, said method comprising the steps:

(a) contacting at a pH of about 4.1 the specimen composition with a first reagent composition containing 4.1 millimoles/liter of uranyl acetate to precipitate protein-bound glucose without denaturing it to produce (i) a precipitate product comprising protein-bound glucose that can be redissolved and that is substantially free of the one or more interfering substances and (ii) a supernatant containing the one or more interfering substances;

(b) separating the precipitate product from the supernatant; and (c) dissolving the precipitate product to give a solution of redissolved protein-bound glucose that is substantially free of the one or more interfering substances while contacting the redissolved protein-bound glucose in solution at a pH of at least about 10.0 with a colorimetric reagent that colorimetrically indicates the presence of protein-bound glucose.

11. The method of claim 10 wherein the colorimetric reagent comprises benzyl viologen and methyl viologen.

12. A method of determining whether an individual has diabetes that utilizes both the protein-bound glucose value and the glucose value for the individual, even if a specimen composition from the individual used for determining the protein-bound glucose value contains one or more interfering substances that may interfere with the determination of the protein-bound glucose value, said method comprising the steps:

(a) obtaining from the individual a specimen composition that contains protein-bound glucose and also contains one or more interfering substances that may interfere with a subsequent assay for protein-bound glucose;

(b) contacting at a pH of about 4.1 the specimen composition with a first reagent composition containing about 4.1 millimoles/liter of uranyl acetate to precipitate protein-bound glucose without denaturing it to produce (i) a precipitate product comprising protein-bound glucose that can be redissolved and that is substantially free of the one or more interfering substances and (ii) a supernatant containing the one or more interfering substances;

(c) separating the precipitate product from the supernatant;

(d) dissolving the precipitate product to give a solution of redissolved protein-bound glucose that is substantially free of the one or more interfering substances;

(e) contacting the redissolved protein-bound glucose in solution at a pH of at least about 10.0 with a colorimetric reagent that colorimetrically indicates the presence of protein-bound glucose to determine the protein-bound glucose value for that individual;

(f) determining the glucose value for that individual; and (g) determining whether that individual has diabetes using both the protein-bound glucose value and the glucose value for that individual.

13. The method of claim 12 wherein the one or more interfering substances are selected from the group consisting of uric acid, bilirubin, glutathione, ascorbic acid, and its metabolites.

14. The method of claim 12 wherein the protein-bound glucose is principally glycated albumin.

15. The method of claim 12 wherein the colorimetric reagent comprises an electron acceptor.

16. The method of claim 15 wherein the electron acceptor is selected from the group consisting of benzyl viologen and methyl viologen.

17. The method of claim 15 wherein the colorimetric reagent comprises benzyl viologen and methyl viologen.

18. The method of claim 12 wherein step (b) is conducted at room temperature.

19. The method of claim 12 wherein step (d) is carried out at about 37° C.

20. The method of claim 12 wherein steps (d) and (e) are performed simultaneously.

21. A method of determining whether an individual has diabetes that utilizes both the protein-bound glucose value and the glucose value for the individual, even if a specimen composition from the individual used for determining the protein-bound glucose value contains one or more interfering substances that may interfere with the determination of the protein-bound glucose value, the interfering substances being selected from the group consisting of uric acid, bilirubin, glutathione, ascorbic acid, and its metabolites, said method comprising the steps:

(a) obtaining from the individual a specimen composition that contains protein-bound glucose and also contains one or more interfering substances that may interfere with a subsequent assay for protein-bound glucose;

(b) contacting at a pH of about 4.1 the specimen composition with a first reagent composition containing 4.1 millimoles/liter of uranyl acetate to precipitate protein-bound glucose without denaturing it to produce (i) a precipitate product comprising protein-bound glucose that can be redissolved and that is substantially free of the one or more interfering substances and (ii) a supernatant containing the one or more interfering substances;

(c) separating the precipitate product from the supernatant;

(d) dissolving the precipitate product to give a solution of redissolved protein-bound glucose that is substantially free of the one or more interfering substances;

(e) contacting the redissolved protein-bound glucose in solution at a pH of at least about 10.0 with a colorimetric reagent that colorimetrically indicates the presence of protein-bound glucose to determine the protein-bound glucose value for that individual, the colorimetric reagent comprising benzyl viologen, or methyl viologen, or both;

(f) determining the glucose value for that individual; and (g) determining whether that individual has diabetes using both the protein-bound glucose value and the glucose value for that individual.

* * * * *